United States Patent
Nakatsu et al.

(10) Patent No.: US 8,685,379 B2
(45) Date of Patent: Apr. 1, 2014

(54) FUNCTIONAL MATERIAL AND DELIVERY GEL COMPOSITION AND METHOD FOR MANUFACTURING

(75) Inventors: Tetsuo Nakatsu, Armonk, NY (US); Ichiro Kubota, Tochigi (JP); Tomonobu Danno, Osaka (JP)

(73) Assignee: International Art and Science Group, Inc., White Plains, NY (US)

( * ) Notice: Subject to any disclaimer, the term of this patent is extended or adjusted under 35 U.S.C. 154(b) by 0 days.

(21) Appl. No.: 12/864,015

(22) PCT Filed: Jan. 29, 2009

(86) PCT No.: PCT/US2009/032497
§ 371 (c)(1), (2), (4) Date: Sep. 28, 2010

(87) PCT Pub. No.: WO2009/097467
PCT Pub. Date: Aug. 6, 2009

(65) Prior Publication Data
US 2011/0027212 A1    Feb. 3, 2011

Related U.S. Application Data

(60) Provisional application No. 61/024,397, filed on Jan. 29, 2008.

(51) Int. Cl.
*A61L 9/04* (2006.01)
*A61L 9/01* (2006.01)
*C08L 1/00* (2006.01)

(52) U.S. Cl.
USPC ............ 424/76.4; 424/76.1; 524/80

(58) Field of Classification Search
None
See application file for complete search history.

(56) References Cited

U.S. PATENT DOCUMENTS

| | | | | |
|---|---|---|---|---|
| 2,367,678 | A | * | 1/1945 | Hatch et al. .............. 106/150.2 |
| 5,380,521 | A | | 1/1995 | Saihara et al. |
| 5,902,572 | A | * | 5/1999 | Luebbe et al. ................ 424/66 |
| 6,180,092 | B1 | | 1/2001 | Lagin |
| 6,509,022 | B2 | | 1/2003 | Lowry et al. |
| 2002/0041860 | A1 | * | 4/2002 | Requejo ..................... 424/76.1 |
| 2002/0055562 | A1 | * | 5/2002 | Butuc .......................... 524/80 |
| 2003/0068295 | A1 | * | 4/2003 | Rohde et al. ................ 424/76.1 |
| 2005/0282755 | A1 | * | 12/2005 | Hart et al. ..................... 514/14 |
| 2007/0166341 | A1 | * | 7/2007 | Nakatsu et al. .............. 424/405 |

OTHER PUBLICATIONS

PCT Appln. Serial No. PCT/US09/32497 filed Jan. 29, 2009.
U.S. Appl. No. 61/024,397, filed Jan. 29, 2008.
Wo 2009/097467 A3—International Search Report 3 pages.

* cited by examiner

*Primary Examiner* — Robert A Wax
*Assistant Examiner* — Randeep Singh
(74) *Attorney, Agent, or Firm* — Andrew F. Young, Esq.; Lackenbach Siegel, LLP

(57) ABSTRACT

The present invention relates to a high concentration functional material gel composition and effective delivery composition thereof. More specifically, the present invention relates to a high concentration functional material gel composition comprising a small organic molecule having at least one of a carbonyl group and at least one of an isolated hydroxyl group from the carbonyl group as a defined mandatory element holding and delivering amounts of functional materials. This is achieved without depending on employing additional incompatible materials in the functional composition, including for example inorganic salts, polymers, absorbents petroleum waxes, and paraffin hydrocarbons.

4 Claims, No Drawings

FUNCTIONAL MATERIAL AND DELIVERY GEL COMPOSITION AND METHOD FOR MANUFACTURING

CROSS REFERENCE TO RELATED APPLICATIONS

This application claims priority from U.S. Ser. No. 61/024,397 filed Jan. 29, 2008, the entire contents of which are herein incorporated fully by reference. This application also claims priority from PCT/US2009/032497 filed Jan. 29, 2009, the entire contents of which are herein incorporated fully by reference.

BACKGROUND OF THE INVENTION

1. Field of the Invention

The present invention relates to a high concentration functional material gel composition and effective delivery composition thereof. More specifically, the present invention relates to a high concentration functional material gel composition comprising a small organic molecule having at least one of a carbonyl group and at least one of an isolated hydroxyl group from the carbonyl group as a defined mandatory element holding and delivering amounts of functional materials. This is achieved without depending on employing additional incompatible materials in the functional composition, including for example inorganic salts, polymers, absorbents petroleum waxes, and paraffin hydrocarbons.

2. Description of the Related Art

The related art involves a conventional small organic functional material composition, hereinafter referred to broadly as a functional composition, is most likely liquid or oil because the composition contains substantially all small (low weight) organic molecules, which have a molecular weight of less than approximately 500 and which have a lower melting point than an ambient temperature range, namely a melting point lower than about 4 C. Ambient temperatures are suggested to be between about 10 C/50 F to about 38 C/100 F with a normal average of approximately 25° C./77 F as a conventional room temperature.

Conventionally related functional material compositions also comprise single molecules, in other word, monomers.

One popular small molecular functional composition is an aromatic functional composition which has a variety of benefits and functions. For example, an aromatic functional composition may provide a pleasant sensation; enhance mood; cover (or mask) for a bad odor, and organoleptically neutralize (or quench) mal-odor, including urine odors and unpleasant odors like "musty-odors" and "garbage-origin" odor; or to control growth of microorganisms.

Another small molecular functional composition is a cleaning functional composition to remove greasy materials including a variety of oils, glue, gum, paint, and dirt.

There are a few contradictions between an aromatic functional composition and target objects. For example, when applied, an aromatic functional composition to enhance and improve mood quickly disappears from the range of a human organoleptic system because of its volatile characteristics—it can no longer be smelled. For example, sprayed aromatic functional compositions applied over cat litter to control mal-odor from waste is superficial and only a temporary solution to cover the urine odor because the urine odor is continuously generated by and emerging from the litter until removed. A mal-odor from a mold on a wall is persistent until the mold is physically or chemically removed. A mal-odor from deteriorating food in garbage is persistent until the garbage is cleaned. A mal-odor from the water system like toilet or sewage is persistent because of frequent uses and continuously supplied mal-odor-source, i.e. urine, and fills up its proximity. Thus, simple covering odors are ineffective.

No practical functional composition or system is disclosed to control effectively, constantly and on-demand such mal-odors in between a human organoleptic system and a mal-odor source, to deliver easily mood enhancing function on-demand to the user; or to remove easily and clean a variety of both oily and water soluble deposits, dirt and taints without giving adverse and/or harmful effect, including mal-odor, irritation and toxicity.

Although there are systems such as fragrance sprays and scented candles that may provide a short-lived result, none is fully effective and satisfactory, or long lasting to provide neutralizing urinal odor when used because the conventional methods have inherent drawbacks.

One drawback is that the fragrance is dispersed broadly, without considering mal-odor emerging direction. Additionally as a concern a human organoleptic system adapts easily and quickly any odor. In other word, even excessively-used fragrances are useless to control mal-odor after several applications due to loss of organoleptic sensation.

On the other hand, it is well known that fragrance oils may change and/or enhance moods. For example, a lavender scent may provide a relaxed mood and a citrus scent may provide an exciting mood. To receive such affects the closer smelling using portable personal type composition, the more efficient can be obtained and the less fragrance in the environment is needed without wasting aromatic functional materials.

Another mal-odor source is wet and muddy and watery areas filled with such rotten materials, microorganism, garbage, food staffs and waste materials including urine or stool. The mal-odors from these sources are strong and persistent. Nevertheless one of the best temporary methods to cover such mal-odors is to simply apply a quenching substance—the detriment being the need for constant reapplication that has here to for remained unrecognized.

One example used in a water system is sublime chemicals, naphthalene and camphor that have very strong unpleasant odor and are considered toxic and carcinogenic. Another example used in a water system is a solid crystalline toilet-ball generally comprising surfactants and fragrances—unfortunately these types of crystalline balls cannot be left in the water because they dissolve in the water and quickly drain.

A cat litter and a urinal pot that are popular in homes and medical facilities are strong mal-odor sources. One example used in a cat litter is disclosed in US Patent 2007-0181071, the entire contents of which are herein fully incorporated by reference, which uses gypsum and soda ash which is inorganic and incompatible material with organic molecules and fragrance materials. In addition, in-house testing with soda or sodium bicarbonate may worsen urine odor via chemical reaction.

An aromatic functional composition is generally oil or liquid that is the most difficult form to be carried and control in a dispersion rate. Shimizu et. al. JP Laid-Open Patent JP2002065820, the entire contents of which are fully incorporated herein by reference, discloses an oily gelled aromatic composition using 12-hydroxystearic acid, paraffin wax, fatty acid amide or substituted urea compound and volatile hydrocarbon to make a gel aromatic composition or fragrance. Shimizu's composition includes at least biodegradable non-sustainable paraffin waxes and more importantly VOC suspected hydrocarbons.

Mori and Ochi, JP Laid-Open Patent JP61012613, the entire contents of which are fully incorporated herein by reference, discloses a gelatinous aromatic composition including 12-hydroxystearic acid and a relatively volatile paraffinic oily perfume, wherein paraffinic oily perfume comprises lower boiling point paraffin (petroleum hydrocarbon) and aromatic materials.

An all-purpose cleaner is becoming more and more critical to increase quality of life, e.g. hygienic quality of life to prevent a variety of diseases. A traditional way for cleaning dirt, especially oily dirt is to use surfactant. Wherever a large amount of water is available and it is appropriately drained into the sewage, the traditional cleaning method will work to clean the dirt. However, water cannot be applied always or is not practical in a variety of dirty objects, e.g. electric appliances and electronic apparatus.

Traditionally, volatile organic compounds or solvents, including toluene, xylene and limonene, even halogenated compounds in dry cleaning, have been used to remove oily dirt, including exhaust pollutants, wet paint, candle waxes, motor oil and oil base glue. All these solvents are considered neurotoxic (act as a neurotoxin) and/or carcinogenic and environmentally harmful materials under VOC (volatile organic compound) regulation. Accordingly, these are restricted and controlled substances to be used on human. In addition, these solvents have strong intolerable unpleasant odor and/or mal-odor, and cause nausea and headache.

A few fatty acid esters, including non-volatile isopropyl myristate (IPM) and dioctylate, have also solvation ability with resolving organic molecules as described above. DE Patent 4,136,811, the entire contents of which is herein fully incorporated by reference, discloses the formulation of a skin cleanser to remove paint on a hand including IPM and alcohol that is volatile and considered also health hazardous. All these small molecular cleaning functional materials are in liquid form and all are either sprayed or applied with cloth or brush. Any liquid form cleaner application has a few serious common drawbacks. These drawbacks include spreading and quickly and widely over the target object and dripping from the target object to cause secondary taints, while cleaning such an old label on a bottle or a poster glued on the wall. In addition, any liquid form requires a special handling and not considered portable. DE '811 did not provide any gel form.

One commercial gel product having IPM is being sold on line http://www.getspfx.com/IPM-Gel.asp, but does not disclose any detail but non-used gel agents Carbosil and TS100 inorganic silica acid base gel agent and to be applied to mouth and eye to remove chewing gum. Another reference GB Patent 2,400,374, the entire contents of which are incorporated fully by reference, is a liquid chewing gum remover containing 50% of D-limonene considered as VOC.

Another drawback of these organic solvent cleaning composition is that the composition cannot remove water soluble taint, including starch base glue and many residual food staff, including carbohydrates, amino acids, and salts. Accordingly, it is considered not all-purpose cleaner and is among those compositions that are not responsive to the concerns resolved by the present invention.

SUMMARY OF THE INVENTION

Until today, a variety of related disclosures noted the use of 12-hydroxystearic acid or hardened castor oil (include 12-hydroxystearic acid as main) to prepare products. However, any related disclosure has failed to recognize the important property that this composition both molecularly holds and also delivers the functional material effectively and gradually when prepared in the manner and composition suggested herein.

The inventors focused on the structural characteristics of the holding-delivery functional material base materials and discovered that there is common structural characteristics, wherein at least one of a carbonyl group and at least one of an isolated hydroxyl group from the carbonyl group, have common appearances as a solid form like crystal, powder and flake at ambient temperature and an excellent crystalline-forming property, and can provide dual functions in a variety of application environments and purposes including air, water, and material surface.

More specifically, the present invention provides a variety of compositions that are able to hold significant amounts of small aromatic organic functional materials and to delivery these organic functional materials on-demand in a variety of environments with user friendly, sustainable and non-toxic materials.

The present invention provides a gel functional composition and a function delivery composition. Further specifically, the present invention provides a gel aromatic functional composition and an all-purpose cleaning composition with portable, easily applicable, inexpensive, non-toxic, and more importantly user and environmentally friendly properties with utilizing minimum natural resources, and the system applicable easily and portably to almost any mal-odor sources and taints.

Even more specifically, the present invention provides to a high concentration functional material gel composition and an effective delivery composition thereof that is readily formable into commercially desirable shapes, maintains a cost effective formulation, allows the use of sustainable and renewable resources, and usable in a solid gel form, a gel granulated form, a paste form, or a soft gel form without employing additional form-enabling materials. Examples of form-enabling materials include a variety of quarterly ammonium materials, biodegradable surfactants, inorganic salts, polymers, petroleum waxes and suspected VOC (volatile organic compound) materials. The proposed material may be readily employed in conventional consumer quantities and enter the commercial water system without concern (e.g. toilet basin, cat litter, and urinal etc.).

The above, and other aspects, features, and advantages of the present invention will become apparent from the following description read in conjunction with the accompanying drawings, in which like reference numerals designate the same elements.

BRIEF DESCRIPTION OF THE DRAWINGS

There are no drawings for the disclosure.

DETAILED DESCRIPTION OF EMBODIMENTS

Reference will now be made in detail to several optional embodiments of the invention.

In coping with the problems noted above, the present invention provides a system for manufacturing a high concentration functional material composition and effective delivery composition thereof (hereinafter referred to functional composition), the functional compositions that replace conventional functional material delivery composition.

In general, a gel composition, including not only a rigid/firm form but also powder, granules, soft gel and tablet forms but not limited thereto, is more convenient to be transported and be applied in practice. The inventors screened a variety of substances and properties including such as those substances solid at room temperature; highly lipophilic (oil soluble or affinitive to volatile materials) and partially hydrophilic property now recognized as being able to hold a rather large amount of organic small molecules with biodegradable, user friendly, air-phase environmentally friendly property; water-phase environmentally friendly property to avoid side effects and secondary concerns like clotting in water systems; further without compromising olfactory-friendly property which will not decrease pleasantness of aromatic composition, including fragrance and essential oils; an excellent crystalline-forming property; easy and effective delivery of functional materials and outstanding cleaning capability.

According to one aspect of the present invention, a gel and/or solid functional composition comprises a critical and mandatory holding-delivery base material at an ambient temperature comprising at least one molecule, shown in general Formulas (1) or (2) below, which have a carbonyl group and a hydroxyl group, and have at least one carbon atom between the carbon atom with ketone and another carbon atom with hydroxy group which may provide both intra-molecular and inter-molecular hydrogen bonding or either; which is a monomer; which is biodegradable and/or environmentally friendly with oxygen atoms in its molecule, which may hold functional materials at least 5% by weight of the total composition; and which may deliver and release functional materials constantly, adequately and on-demand from the total composition thereof.

Hydrogen boding is well known and studied in pure chemistry and composition chemistry. However, an interaction in outside environments like in air and water is unknown and far from certain. The present invention can provide a means to optimize creation to achieve a desirable holding-delivery property of material compositions, which can satisfy needs without using additional and/or specific device.

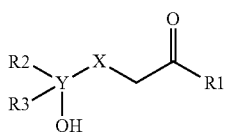

Formula (1)

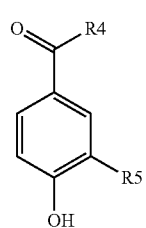

Formula (2)

In alternatively desirable aspect of the present invention, one or more of the above noted holding-delivery base materials is selected one from the group represented with Formula (1); specifically, wherein (A) R1=OH, X=(CH2)9, Y=C, R2=(CH2)5CH3 and R3=H [as represented by 12-hydroxy-stearic acid shown in Formula (3) below]; (B) R1=OH, X=Y=C, R2=COOH and R3=CH2COOH [as represented by citric acid shown in Formula (4) below]; and wherein (C) R1=CH3, X=CH2, and Y=para-C6H6 (or benzene ring) including R2 and R3 [as represented by a raspberry ketone shown in Formula (5) below], but not limited to the above molecules, if a molecule is represented by Formula (1).

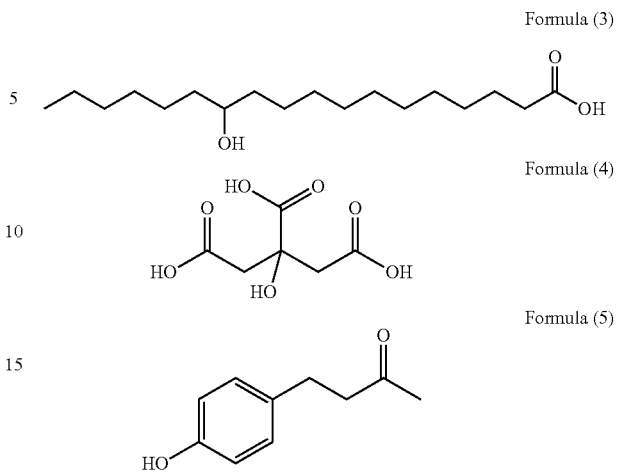

In another alternatively desired aspect of the present invention, one or more of the above noted holding-delivery base materials is selected one from the group represented with Formula (2); specifically, wherein: (A) R4=H and R5=OCH3 [as exemplified in vanillin], (B) R4=H and R5=OCH2CH3 [as exemplified in ethylvanillin], and (C) wherein R4=OCH3 and R5=H (as exemplified in methyl-4-hydroxybenzoate (paraben)].

All selected embodiments as the above have an excellent crystalline-forming property at ambient temperature. It is noted that the phrase 'gel' is to be interpreted liberally meaning 'non liquid', such that a gel may be a solid, amorphous or non-amorphous (partially or wholly crystalline) or may be a flexible solid like a gel-based composition.

A concentration of one or more of the above noted holding-delivery base materials are in the range of 1% to 95% by weight, and preferably, 2% to 80% and more preferably 3% to 50%.

It will be additionally recognized that the functional material may be selected from a wide group of materials including: an organic molecule; aromatic oil, fragrance; liquid-base remover, liquid-base cleaner, antibacterial, preservative, stabilizer, foaming agent, anti-mollusk, anti-fungous, anti-termite, anti-algae, anti-oxidation, anti-mosquito, and anti-feeding agents; insect repellant; herbicide; fertilizer; soil conditioner and water conditioner, an emollient, a fertilizer, an anti-bacterial material, an insecticide, and isopropyl myristate (IPM) as the ester of isopropanol and myristic acid.

EXPERIMENTAL EMBODIMENTS

A benefit of the present invention is further provided in the following Embodiments.

Embodiment 1

12-Hydroxy-stearic acid is being used to solidify the vegetable oils and to make clear candle, and also used in a variety of cosmetic composition as a firming agent. All compositions were heated and poured to a metal plate. Each weight was measured to calculate a relative ratio for aromatic function delivery composition. Comparison Sample 1, a candle wax (petroleum hydrocarbon wax) and scented candle is being used as an air-freshener. Comparison Sample 2, MC Stearin S (approximately 47% of palmitic acid, 49% of stearic acid and other saturated fatty acid by weight available from Kawaken Fine Chemical Co., Japan and registered as Stearic Acid), have very similar aromatic material delivery property, but the candle wax itself is slightly better than MC Stearin S. Comparison Sample 3 has only 12-hydroxy-stearic acid and Sample 1 is a mixture of 12-hydroxy-stearic acid and MC Stearin S. According to the table 2, it is recognized that addition of 12-hydroxy-stearic acid increases volatile functional material delivery ratio, wherein the chemical structural difference between 12-hydroxy-stearic acid and stearic acid is only if there is an isolated hydroxy group or not, and palmitic acid has no isolated hydroxyl group and two less methylene groups than stearic acid. Additional methylene group is considered generally not significant from chemistry standpoints. Accordingly, it is considered that the hydroxyl group is significant element to increase volatile functional material delivery ratio, also supported by Embodiment 4 of raspberry ketone.

Addition of 12-hydroxy-stearic acid improves appearance of the product and makes a longer lasting aromatic product with higher biodegradability and more affinity property to other ingredients than hydrocarbon petroleum waxes that are not sustainable, a VOC and very hydrophobic and less affinitive to small organic molecules having oxygen and/or nitrogen. Volatile functional material delivery rate can be controlled by changing a ratio between 12-hydroxy-stearic acid and stearic acid.

MC Stearin S sold under Stearic acid, another saturated fatty acid mixture like Triple Pressed Stearic Acid also sold under Stearic Acid containing variable amount of palmitic acid and stearic acid may be used without further concern.

TABLE 1

| Samples | Candle Wax (%), a paraffin wax | HC Stearin S (%) | 12-Hydroxy-stearic acid (%) | Volatile (aromatic) materials concentration (%) |
| --- | --- | --- | --- | --- |
| Sample 1 | | 50 | 34 | 16 |
| Comparison Sample 2 | 89 | | | 11 |
| Comparison Sample 2 | | | 90 | 10 |
| Comparison Sample 3 | | 85 | | 15 |

(%); By weight; Fragrance: Fragrance name: Green tea fragrance comprising 15% of vertenex, 8% of hexylsalcilate, 8% of hedione, 8% of geraniol, 15% of florol, 2.5% of lemon grass oil and the green tea base.

TABLE 2

| Samples | Appearance | Odor strength | Odor quality | Volatile (aromatic) materials delivery (decrease) ratio (after 17 days) |
| --- | --- | --- | --- | --- |
| Sample 1 | Smooth homogenous with no color irregularity | Strong | Very good | 21% |
| Comparison Sample 1 | Very smooth but like wet surface | Weak | Fair | 16% |
| Comparison Sample 2 | Like flour paste with irregular tone in color and appearance | Very strong | Very good | 79% |
| Comparison Sample 3 | Smooth with small irregularity | Very weak | Fair | 11% |

Embodiment 2

Approximately 1.5 g of each Sample was formed into a plastic plate container, round shape with 40 mm diameter and 13 mm thickness) and a inside plate is turnable, which is called Swing-out available from Qosmedix, N.Y. The base materials were melted by heating and then aromatic materials were added to prepare all Samples by pouring onto the plate having a synthetic glue (organic compound base glue like Glue Dots® and Gorilla Glue®), approximately center of the plastic plate. The glue and each composition became solid without dropping from the plate. The container can be closed and opened at will to deliver conveniently aromatic materials on-demand with high portability. Specifically, there is no dripping and leaking of oily non-gel materials which cause a variety of problems due to oily materials when carried in a pocket or a handbag.

Sample 1 in the container was tested on mal-odor neutralizing effect. The results were evaluated by trained or contract testers.

TABLE 3

| Place | Application method | Mal-odor type | Result |
| --- | --- | --- | --- |
| Closed-type closet with a door | Open and placed in close proximity to the door | Musty and earthy | Unpleasant musty odor was not sensed when the closet door is opened. |
| Toilet room | Open and placed in close proximity to the toilet | Heavy urinal ammonium note | Sensing clean and almost no toilet odor when enter. |
| Taxi with smoky odor | Get in a taxi and open Sample where and when smoky. | Smoky cigarette and unpleasant note | The smoky cigarette odor was gone out of organoleptic sensation. |
| Small closed child room | Open and placed in close proximity to the door. | Sweaty and sour note | No particular mal-odor was sensed when the door was opened. |

Embodiment 3

Further, another aroma function holding and delivery composition, Sample 2 comprising the materials provided in Table 4 may provide another preferable stable Embodiment 3 with methyl-4-hydroxybenzoate as a preservative and a secondary holding-delivery base material.

Sample 2

| Material | Percentage by weight (%) |
| --- | --- |
| MC Stearin S | 32.8 |
| 12-Hydroxy stearic acid | 49.2 |
| Methy-4-hydroxybenzoate | 1.6 |
| Fragrance Green tea | 16.4 |

Embodiment 4

Sample 3 is prepared using an insect repellant liquid composition sold in the market. Sample 3 is tested by a contract tester and showed appreciable protective effect from a mosquito.

Sample 3: Solid ball

| Material | Percentage by weight (%) |
| --- | --- |
| MC Stearin S | 29 |
| 12-Hydroxy stearic acid | 50 |
| Methy-4-hydroxybenzoate | 1 |
| d,d-T-80 Prallethrin mixture* | 20 |

*Commercial insecticidal and insect repellant active composition

Embodiment 5

Raspberry ketone characterizing raspberry odor of the fruit was melted and fragrance Refresh (as an aromatic function material) was added. Completely melted mixed liquid was poured to a mold. Approximately 9.3 g of the solid mixture, Sample 4, comprising 88% of raspberry ketone and 12% of fragrance Refresh by weight was immersed in man's toilet drain.

Each weight of the solid composition was measured and mal-odor neutralizing effect was evaluated. After 9 days the solid mixture completely disappeared into the drain. When the user urinated, the fresh aromatic olfactory sensation neutralized the urinal odor sensation, and in addition, when the toilet was flushed after use, further fresh clean sensation emerged from Sample 3 fills up to provide a fresh clean olfactory sensation when a next user entered the room.

Embodiment 6

Raspberry ketone base Sample 4 with fragrance Refresh and Sample 5 with fragrance Kiku were compared with MC Stearin S base Comparison Sample 4 (MC Stearin S and fragrance Refresh), Comparison Sample 5 (MC Stearin S only), Comparison Sample 6 (sodium bicarbonate only) and Comparison Sample 7 (sodium bicarbonate and fragrance Refresh) in urine. Each approximately 200 mg of Samples were put in the glass jar and 5 g of urine was added to each jar The result indicate that raspberry ketone delivers more aromatic functional materials than stearic acid base in the water system. By the way stearic acid, MC Stearin S and 12-hydroxy-steric acid do not dissolve in water even they were exposed for a few months. After aromatic functional materials were gone from both stearic acid and 12-hydroxy-stearic base, a mold began growing. Accordingly, from user convenient standpoints, it is desirable if the products completely disappeared either into the air, the drain or the water environment. In the soil, since the composition of the present invention is highly biodegradable, it will be quickly decomposed by soil bacteria.

TABLE 4

| Terms | Urine odor strength | Impression |
| --- | --- | --- |
| Control (with no chemical) | +++ | Very strong urine odor |
| Sample 4 (Fragrance Refresh) | − | No urine odor |
| Sample 5 (Fragrance Kiku) | ± | No urine odor and strong fragrance characteristics |
| Comparison Sample 4 | +++ | Very strong urine odor |
| Comparison Sample 5 | + | Weaker but remarkable urine odor |
| Comparison Sample 6 | +++ | Very bad strong urine odor |
| Comparison Sample 7 | ± | Weaker but remarkable urine odor |

Fragrance Refresh comprises 15% of galaxolide, 7% of musk T, 23% of linalool, 3% of styralyl acetate, 8% of hedione, 12% of dihydromyrcenol and fresh base. Fragrance Kiku comprise 9% of galaxolide, 4% of triplal, 11% of florol, 22% of hedione, 18% of linalool and kiku base.

Embodiment 7

Sample 4 with the average weight 37.5 g of Embodiment 3 was molded like a cupcake and was tested in practical use for institutional man's rooms. As a commercial toilet cleaning ball from Nissan Chemical, used as a Comparison Sample 8 which is a surfactant base solid product. Sample 4 and Comparison Sample 8 were set in six different men's rooms lactated in different floors of the two premises. Samples and Comparison Samples were set at random inside-bottom of each man's toilet of the same toilet room. All Samples tested were completely disappeared within 5 months. Calculated average daily-decreasing-weights and general user's comments are shown in Table 5. It is obvious that Sample 4 is more acceptably pleasant and credited than the current market leading product.

TABLE 5

| Terms | Sample 4 | Comparison Sample 8 |
| --- | --- | --- |
| Daily decreasing rate range | 0.30 g-0.95 g | 0.76 g-2.0 g |
| Preference by users with covering mal-odor | Covered urine odor and preferred to Comparison Sample | Less covered urine odor and less preferred to Sample |

Embodiment 8

Citric acid is found in citrus fruits and is an important intermediate in the citric acid cycle of human's metabolism. Also it is known to act as an environmentally benign cleaning agent. Citric acid has a rather high melting point at 153° C. Accordingly it is not appropriate to heat the acid with volatile aromatic materials to melt and mold. Thus 45 g of granule citric acid purchased was pulverized and was mixed with 10 g of fragrance Refresh to provide granular Sample 6. The fragrance concentration was 18.2% by weight. Even at this concentration the oil was not apart from the acid in granular form. 2 g of the granular Sample 6 was set at the bottom of a glass jar and approximately 30 g of fresh urine was added. Comparison Sample 9 without any chemical was prepared with the same amount of urine. Both were tested by smelling for a week. Sample 6 was dissolved immediately after the urine was added.

TABLE 6

| Term | Sample 6 | Comparison Sample 9 |
| --- | --- | --- |
| Right after urine was added | No recognizable urine odor | Strong urine odor |
| After 1 day | Almost no odor | Strong |
| After 3 days | No mal-odor, clear yellow-brown solution | Very strong ammonium like bad-odor, turbid |
| After one week | No mal-odor, clear yellow brown solution | Very strong mal-odor like typical unclean toilet odor |

Embodiment 9

2 g of Sample 6 was dispersed over cat litter sand. After a few weeks, there was no recognizable cat urinal or waste odor and the contract testers were pleased. This application provides further benefits because when the composition dissolved in the urine or even when rain both the fragrance and citric acid were adsorbed on the soil of which most abandoned material is silica gel that is used as adsorbent for most organic molecules. As results, the aromatic functional composition would stay longer on or in proximity of the soil surface.

Embodiment 10

Ethylvanillin is formed into Sample 7 composed of 85% of ethylvanillin by weight and 15% of Fragrance Lavender composed of 18% of Musk T, 8% of Iso Super E, 4% of hedione, 15% of linalool, 20% of linalyl acetate, 20% of lavender oil, 4% of rosemary oil, and 11% of floral fragrance base. Sample 7 provide strong pleasant lavender scent with sweet and weak vanilla scent. Sample 7 has slowly degraded into the water system over a couple of month period.

Embodiment 11

Smooth white gel Sample 8 was prepared by following procedures. 3.05 g of 12-hydroxy-stearic acid and 1.04 g of an Amizol® emulsifier, Amizol CME; an amide ester (Kawaken Fine Chemical, Tokyo Japan), were gently heated to melt and 62 g of IPM and approximately 41 g of water added under continuous rather vigorous agitation until cooled down to give a smooth gel formula. Another smooth white gel Sample 9 was prepared using the same method but different content ratio. The gel formula Sample 8 and 9 are easily applied from a tube applicator. Sample 8 and 9 can be applied on the perpendicular wall without dripping for a while.

Comparison Sample 10, Comparison Sample 11 and Comparison Sample 12 have been prepared by mixing IPM, D-limonene and ethyl adipate with melted 12-hydroxy stearic acid (3) and then reheated to give a homogenous clear hot solution. All are cooled down to provide gels.

TABLE 7

| Material | Sample 8 (IPM) | Sample 9 (IPM) | Comparison Sample 10 (IPM) | Comparison Sample 11 (D-Limonene) | Comparison Sample 12 (Ethyl adipate) |
| --- | --- | --- | --- | --- | --- |
| Functional material | 62 g | 300 g | 5.10 g | 5.03 g | 5.34 g |
| 12-Hydroxy stearic acid (3) | 3.05 g | 30 g | 0.25 g | 0.25 g | 0.22 g |
| Concentration of acid (3) | 2.8% | 2.9% | 4.7% | 4.7% | 4.0% |
| Water | 41 g | 700 g | 0 | 0 | 0 |
| Amizol ™ CME | 1.04 g | 0 | 0 | 0 | 0 |
| Amizol ™ CDE | 0 | 10 g | 0 | 0 | 0 |
| Appearance | White soft-smooth gel. Oily on the skin. | White soft-smooth gel. Not oily on the skin. | Semi-clear semi-hard gel. Very oily on the skin. | Semi-clear semi-hard gel. Remove fat from the skin. | Semi-clear gel Semi-hard gel. |
| Odor | Odorless | Odorless | Odorless | Strong odor | Odorless |

Gel Sample 8 and Sample 9, Comparison Sample 10, Comparison Sample 11, Comparison Sample 12 and water were applied old tin-can labels respectively. The results are shown in Table 8.

TABLE 8

| | Removal of an old label with synthetic glue | Starch base glue | General observation |
| --- | --- | --- | --- |
| Sample 8 | Very easy after several minutes and the very small amount of residual glue was easily wiped off. | Easily wiped off. | Very clean easy operation. Little bit oily but very skin friendly |
| Sample 9 | Very easy after several minutes and the very small amount of residual glue was easily wiped off. | Easily wiped off. | Very clean easy operation and very skin friendly |
| Comparison Sample 10 | Very easy after several minutes and the very small amount of residual glue was easily wiped off. | Not wiped off. | No odor, no harmful feeling on the skin and noting is dripped. |
| Comparison Sample 11 | Easily smoothly peeled off the label with recognizable amount of glue deposition after 5 minutes. | Not tested. | Strong citrus odor and caused nausea. |

TABLE 8-continued

| | Removal of an old label with synthetic glue | Starch base glue | General observation |
|---|---|---|---|
| Comparison Sample 12 | The label was not peeled off smoothly and some are remained. | Not tested. | No odor. |
| Water | Almost nothing was peeled off with loosing color on the label. | Easily wiped off. | No odor. |

According to the above detail description and Embodiments, the present invention provides a solid fragrance delivery system in both air and water environment with a variety of portable and convenient forms. Those of skill in the art may form other functional elements including but not limited to antibacterial, preservative, stabilizer, foaming agents, antimollusk, anti-fungous, anti-termite, anti-algae, anti-oxidation, isopropyl myristate (IPM), anti-mosquito, insect repellant, anti-feeding agents, herbicide, fertilizer, and soil conditioner into a composition of the present invention, but not limited to without departing from the scope and spirit of the present invention.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments, if employed at all, is not intended to indicate a desire to invoke the special provision of 35 U.S.C. 112, paragraph 6 to define the invention. To the contrary, if the provisions of 35 U.S.C. 112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. 112, paragraph 6. Moreover, even if the provisions of 35 U.S.C. 112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A functional material and delivery gel composition with water, consisting of:
a gel forming base material, an emulsifier, and at least 16% by weight of a functional material to provide a gel state at an ambient temperature, wherein said gel forming base material is a hydroxy ketone having a general formula (1) or formula (2);

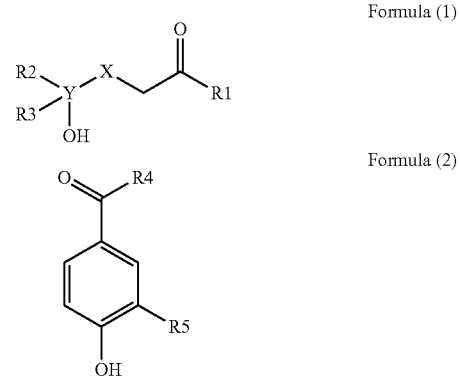

wherein Formula (1) is at least one of:
(A) $R1=OH$, $X=(CH_2)_9$, $Y=C$, $R2=(CH_2)_5CH_3$, and $R3=H$;
(B) $R1=OH$, $X=Y=C$, $R2=COON$ and $R3=CH_2COOH$; and
(C) $R1=CH_3$, $X=CH_2$, and $Y=para-C_6H_6$ including R2 and R3;
wherein optionally Formula (2) is represented by at least one of: (A) $R4=H$ and $R5=OCH_3$; (B) $R4=H$ and $R5=OCH_2CH_3$; and (C) $R4=OCH_3$ and $R5=H$; and
wherein said functional material includes isopropyl myristate (IPM) and contains no antibacterial material, and said functional material and delivery gel composition is formed with the presence of water.

2. A functional material and delivery gel composition, according to claim 1, wherein:
said hydroxy ketone is at least one material selected from the group consisting of:
12-hydroxystearic acid, raspberry ketone, citric acid, vanillin, ethylvanillin, and methyl-4-hydroxybenzoate; and
wherein a concentration of said hydroxy ketone is in the range of 1% to 98% by weight of said composition.

3. A functional material and delivery gel composition, according to claim 1, wherein:
said functional material is selected from the group consisting of an all-purpose cleaner, a chewing gum remover, a glue cleaner and remover, a paint cleaner, a glued object remover, an oil remover, a solid-surface cleaner, and a skin-contact cleaner.

4. A functional material and delivery gel composition, according to claim 1, wherein:
said gel forming base material is a hydroxy ketone having a general formula (1); and
wherein $R1=CH_3$, $X=CH_2$, and $Y=para-C_6H_6$ including R2 and R3,
wherein said functional material is an air freshening fragrance.

* * * * *